(12) United States Patent
Brody

(10) Patent No.: US 10,631,788 B2
(45) Date of Patent: Apr. 28, 2020

(54) DIAGNOSTIC DRAINAGE CATHETER ASSEMBLY AND METHODS

(71) Applicant: SRS Medical Systems, LLC, North Billerica, MA (US)

(72) Inventor: Lee Brody, Somerville, MA (US)

(73) Assignee: SRS Medical Systems, LLC, North Billerica, MA (US)

( * ) Notice: Subject to any disclaimer, the term of this patent is extended or adjusted under 35 U.S.C. 154(b) by 0 days.

(21) Appl. No.: 16/066,478

(22) PCT Filed: Oct. 17, 2017

(86) PCT No.: PCT/US2017/056905
§ 371 (c)(1),
(2) Date: Jun. 27, 2018

(87) PCT Pub. No.: WO2018/075468
PCT Pub. Date: Apr. 26, 2018

(65) Prior Publication Data
US 2019/0216401 A1 Jul. 18, 2019

Related U.S. Application Data

(63) Continuation of application No. 15/695,249, filed on Sep. 5, 2017, now Pat. No. 10,485,483.
(Continued)

(51) Int. Cl.
*A61B 5/00* (2006.01)
*A61M 25/10* (2013.01)
(Continued)

(52) U.S. Cl.
CPC ............ *A61B 5/6853* (2013.01); *A61B 5/036* (2013.01); *A61B 5/04012* (2013.01);
(Continued)

(58) Field of Classification Search
CPC ... A61B 5/6853; A61B 5/036; A61B 5/04012; A61B 5/0488; A61B 5/205; A61B 5/208; A61M 25/10185; A61M 25/0017
See application file for complete search history.

(56) References Cited

U.S. PATENT DOCUMENTS 5,100,394 A 3/1992 Dudar et al.
5,573,007 A 11/1996 Bobo, Sr.
(Continued)

OTHER PUBLICATIONS

International Search Report and Written Opinion from PCT/US2017/056905; 9 pages; Lee W. Young; dated Jan. 8, 2018.

*Primary Examiner* — Paula J Stice
(74) *Attorney, Agent, or Firm* — Dicke, Billig & Czaja, PLLC

(57) ABSTRACT

A vesical pressure measurement system is provided. One or more elements of the system are operably combinable with a previously deployed urinary drainage catheter. The system includes a urodynamic data system and a urinary drainage catheter balloon adaptor. The data system is characterized by a pressure sensor for vesical pressure measurement, and a processor/controller for receiving, processing and/or displaying select urodynamic patient parameters comprising sensed/monitored pressure data. The adaptor operably unites the pressure sensor of the data system to a balloon inflation valve of the catheter. The adaptor includes an adaptor valve for connection to the balloon inflation valve, and a housing, the housing including a balloon inflation valve portion and an adaptor valve portion, the portions urgingly uniteable in furtherance of establishing and maintaining a secure interface between the balloon inflation valve and the adaptor valve.

35 Claims, 7 Drawing Sheets

Related U.S. Application Data

(60) Provisional application No. 62/510,759, filed on May 25, 2017, provisional application No. 62/467,520, filed on Mar. 6, 2017, provisional application No. 62/408,908, filed on Oct. 17, 2016.

(51) Int. Cl.
*A61B 5/0488* (2006.01)
*A61B 5/03* (2006.01)
*A61M 25/00* (2006.01)
*A61B 5/04* (2006.01)
*A61B 5/20* (2006.01)

(52) U.S. Cl.
CPC ............ *A61B 5/0488* (2013.01); *A61B 5/205* (2013.01); *A61M 25/0017* (2013.01); *A61M 25/10185* (2013.11); *A61B 5/208* (2013.01)

(56) References Cited

U.S. PATENT DOCUMENTS

| | | |
|---|---|---|
| 5,617,876 A | 4/1997 | Van Duyl |
| 5,916,153 A | 6/1999 | Rhea, Jr. |
| 5,951,497 A | 9/1999 | Wallace et al. |
| 5,984,879 A | 11/1999 | Wallace et al. |
| 6,021,781 A | 2/2000 | Thompson et al. |
| 6,434,418 B1 | 8/2002 | Neal et al. |
| 6,447,462 B1 | 9/2002 | Wallace et al. |
| 7,004,899 B2 | 2/2006 | Tracey |
| 7,766,870 B2 | 8/2010 | Dabbs |
| 8,192,368 B2 | 6/2012 | Woodruff et al. |
| 8,337,411 B2 | 12/2012 | Nishtala et al. |
| 8,535,237 B2 | 9/2013 | Nishtala |
| 2006/0276712 A1 | 12/2006 | Stothers et al. |
| 2007/0010761 A1 | 1/2007 | Mo |
| 2009/0221933 A1 | 9/2009 | Nishtala et al. |
| 2012/0041334 A1 | 2/2012 | Goedje et al. |
| 2013/0267868 A1 | 10/2013 | Connors et al. |
| 2016/0183819 A1 | 6/2016 | Burnett et al. |

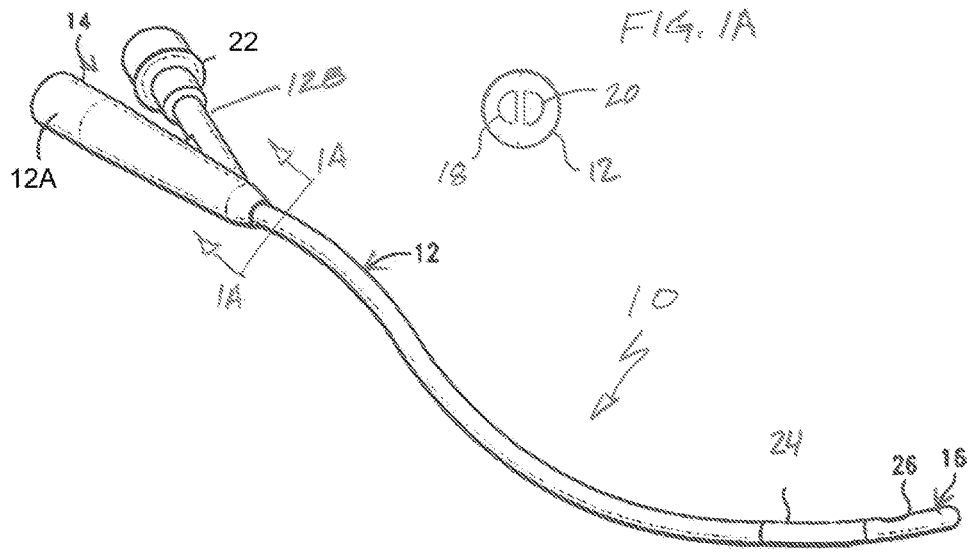
FIG. 1
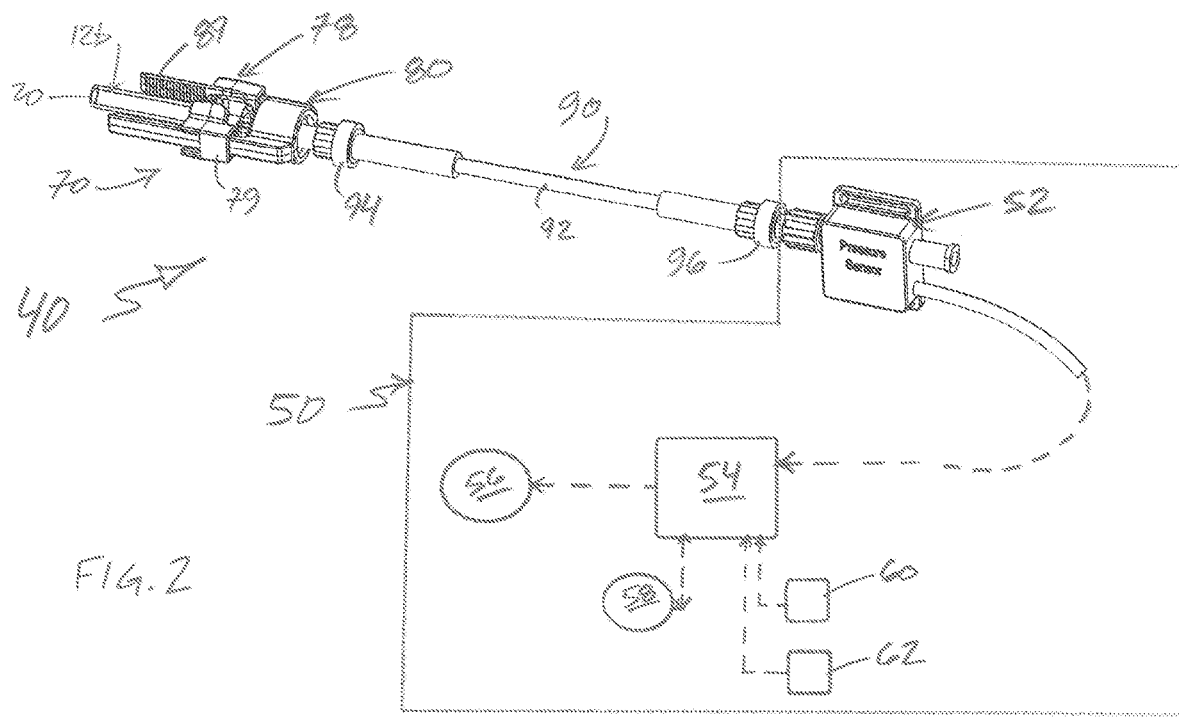

DIAGNOSTIC DRAINAGE CATHETER ASSEMBLY AND METHODS

CROSS-REFERENCE TO RELATED APPLICATIONS

This utility patent application is a U.S. National Stage filing under 35 U.S.C. § 371 of application Ser. No. PCT/US2017/056905, filed Oct. 17, 2017, which is an international patent application filed under 35 USC § 363 claiming priority under 35 U.S.C. § 119(e) to the U.S. patent application Ser. No. 15/695,249 filed Sep. 5, 2017 pursuant to 35 USC § 111(a) claiming priority under 35 USC § 120 of/to U.S. Pat. Appl. Ser. No. 62/510,795 filed May 25, 2017, U.S. Pat. Appl. Ser. No. 62/467,520 filed Mar. 6, 2017, and U.S. Pat. Appl. Ser. No. 62/408,908 filed Oct. 17, 2016, each entitled DIAGNOSTIC DRAINAGE CATHETER ASSEMBLY, the disclosures of which are hereby incorporated by reference in their entireties.

TECHNICAL FIELD

The present invention is generally directed to one or more of kits, systems, assemblies, subassemblies, apparatuses, devices, and/or methods for/of measuring/obtaining bladder vesical pressure using a urinary drainage catheter, more particularly still, to any of such items and/or methods characterized by use of a balloon fluid fill port of a urinary drainage catheter to ascertain vesical pressure and the like, with a urodynamic assessment methodology and attendant, advantageous, non-limiting system likewise provided, and further still, to a protocol for determining indwelling urinary catheter removal parameters and/or conditions.

BACKGROUND

A urinary catheter is a hollow, partially flexible tube that permits the free passage or drainage of urine from the bladder for external collection via a drainage bag or the like. The catheter is inserted into an individual's bladder via the urethra, effectively short circuiting the anatomy/physiology of the lower urinary tract (i.e., creates a low resistance channel to passively drain the bladder, often to an external urine collection device). The catheter may be one that stays in place throughout the day (i.e., an indwelling urinary catheter commonly characterized by a bladder anchor structure, e.g., an inflatable balloon), or an intermittent catheter which is inserted and removed each time the bladder is drained.

Catheters are utilized for several different clinical reasons such as urinary incontinence (i.e., leaking urine or being unable to control when you urinate), or following lower urinary tract surgery in which the surgeon is looking to avoid filling the bladder and/or having the urine come in contact with the urethra immediately following a medical procedure. More usually, a urinary catheter is utilized when a patient has symptoms of urinary retention (i.e., being unable to empty your bladder when you need to), a medical condition, or surgery. Excessive urine accumulation in the bladder may cause pain, bladder injury and/or reflux of urine through the ureters into the kidneys.

Most catheters are a short term fix (i.e., temporary), necessary only until the ability to self-void can be reliably and safely demonstrated, however, circumstances abound which warrant a lengthy deployment (i.e., chronic).

Each year in the United States, more than a million patients receive an indwelling urinary catheter due to urinary retention. Urinary retention often occurs when the bladder vesical pressure does not adequately overcome the bladder outlet resistance, resulting in an inability to adequately empty the bladder. These episodes are often temporary and the drainage catheter can eventually be removed. Many of these retention events occur in hospitals as a result of temporary impairment of vesical pressure.

Hospitals and urology practices have difficultly predicting when an individual no longer needs a urinary catheter to empty his or her bladder. The use of urinary catheters comes with a high incidence of medical complications, including urinary tract infections, known as catheter associated urinary tract infections (CAUTIs), the most common type of healthcare associated infection. Traditionally, caregivers may have erred on the side of leaving the catheter in too long, resulting in high rates of CAUTIs. The Centers for Disease Control and Prevention (CDC) estimates 13,000 U.S. patient deaths each year due to CAUTIs, an excess length of stay of two to four days, an unnecessary antimicrobial use, and an increased cost of $0.4-0.5 billion nationally per year ("Catheter-associated Urinary Tract Infection (CAUTI) Toolkit," Carolyn Gould, MD MSCR).

Due to an increased awareness of catheter-related medical complications and various emerging healthcare economic incentives, including financial penalties directly tied to rates of CAUTIs, the protocols for the removal of urinary catheters have become more aggressive and have resulted in increased incidents of bladder injury due to retention events after premature removal of the urinary catheter.

There are a wide range of clinical protocols to determine whether a catheter can be removed, often dependent on place-of-service and whether a urologist is involved in the protocol. These varying protocols commonly involve the removal of the catheter without an assessment of vesical pressure; the bladder is simply allowed to fill, either naturally or artificially, and observations over time as to whether the patient remains in urinary retention are made, with a bladder ultrasound oftentimes used to measure post void residual urine remaining in the bladder. If the patient cannot adequately void, a catheter is again placed in the bladder. This is an expensive protocol, requiring highly organized and lengthy clinical supervision to determine whether the catheter needs to be replaced. Complications of this protocol include inadvertent overfilling of the bladder during retention events (i.e., bladder distention) as well as the known increase in CAUTI risk owing to the process of reinserting a catheter that was prematurely removed.

As was previously referenced, bladder vesical pressure determinations and assessment are important indicators of lower urinary tract functionality, and a critical component of a urodynamic study. The measurement of bladder vesical pressure using a standard indwelling (Foley) drainage catheter deployed for that purpose is currently a gold standard for the diagnosis of intra-abdominal hypertension (IAH) and abdominal compartment syndrome (ACS). Historically, Foley catheters have been specifically deployed and utilized to measure vesical pressure as part of a urodynamics examination for various assessments of bladder dysfunction.

The Foley catheter, named for its designer Boston surgeon Frederic Foley, is by far the most common type of indwelling urinary catheter. For all intents and purposes, the Foley catheter is the standard-of-care device to address retention.

With reference to FIG. 1, Foley catheter 10 generally comprises a body 12 (e.g., tube) characterized by proximal 14 and distal 16 end portions, and two discrete channels or lumens, namely, a drain lumen 18, and an inflation lumen 20 (FIG. 1A).

Proximal portion 14 of tube 12 is characterized by a bifurcation which delimits a drain segment 12A, characterized by lumen 18, and an inflation segment 12B, characterized by lumen 20. Drain segment 12A is adapted for operative union with a urine collection system, commonly a urine collection device and a valve for regulating urine discharge/collection. Inflation segment 12B is adapted to include an inflation valve 22.

Distal portion 16 of tube 12, the insertion end, includes an anchoring structure in the form of an inflatable balloon 24. Balloon 24 is operatively linked to inflation valve 22 via lumen in furtherance of select inflation (i.e., expansion) of the inflatable balloon, commonly with sterile water, once distal end portion 14 is suitably positioned in the bladder. Moreover, distal portion 16 of tube 14 includes a urine ingress port in the form of an aperture 26 in a sidewall of tube 12, with drain lumen 18 terminating at or combining with the aperture so as to delimit and function as a urine conduit, draining urine from the bladder to and into the external collection bag.

In bladder pressure related assessment applications, a standard 2-way or 3-way Foley catheter is placed into the bladder, the former characterized by one balloon fill port and one urine drainage port, the latter by one balloon fill port and two urine drainage ports. Fluid, commonly sterile water, is introduced into the anchoring balloon to enable retention of the device via cooperative engagement of the fluid filled balloon with the bladder outlet/bladder neck.

Depending on the clinical application, the bladder may be artificially filled with fluid, often sterile water, through the drainage line of the catheter. A pressure transducer is connected to the urine drainage line to indicate/measure the vesical pressure. The pressure transducer may be designed to prevent urine from draining through the urine drainage line, thus, a 3-way catheter is often chosen for continuous monitoring as drainage can continue to occur through the primary drainage line.

In the application of the diagnosis of IAH or ACS, continuous monitoring of the vesical pressure provides insight into the state of the intra-abdominal pressure. Typical clinical applications include emergency trauma and acute care surgery patients who are at risk of IAH and resultant organ dysfunction. In the application of assessment of bladder dysfunction, the vesical pressure is often monitored while the bladder is being filled, and when the bladder is emptying through the catheter.

Numerous catheters beyond the basic Foley, and adaptations thereof, have emerged for the assessment of bladder storage anomalies (i.e., incontinence), including attendant devices/systems that enable multifunction operation. More particularly, functionally specific specialty catheters are available to perform urodynamic assessments.

For instance, Rhea, Jr. (U.S. Pat. No. 5,916,153) generally provides a multifunction catheter, more particularly, a Foley catheter adapted to include an integral pressure sensor near the insertion end thereof. The sensor is embedded or molded into the catheter wall, with associated wiring extending from the sensor embedded in the catheter structure.

Neal et al. (U.S. Pat. No. 6,434,418), as Rhea, Jr., likewise provide a multifunction catheter, more particularly, a modified Foley catheter for measuring intrauterine pressure and fetal heart rate. Three embodiments of this specialized catheter are disclosed by Neal et al., each characterized by one or more of a fetal heart rate electrode proximal an insertion end (see Neal et al. FIG. 2), a pressure sensor proximal an insertion end (FIG. 5 (Neal et al.)), or a microphone proximal an insertion end (FIG. 7 (Neal et al.)).

A pressure transducer and output device are operatively linked to the catheter for sensing bladder pressure via the anchor balloon and its associated lumen (FIG. 1 (Neal et al.)), or via a dedicated pressure sensor (FIG. 5 or FIG. 7 (Neal et al.)).

Wallace et al. (U.S. Pat. No. 6,447,462) provide a urodynamic catheter system characterized by a small volume, closed air column operatively linking a catheter anchoring balloon with a remote transducer assembly. Provisions for a catheter employing a transducer external to a patient's body which does not rely upon a liquid filled column and which provides an automatic reference pressure is a stated aim.

Tracy (U.S. Pat. No. 7,004,899), in keeping with Rhea, Jr. and/or Neal et al., make use of specially equipped Foley catheters while generally providing a portable self-contained diagnostic system for assessing urinary function characterized by a control device adapted to receive a plurality of testing modules (see FIG. 5, and compare FIGS. 1 & 2). A cystometrogram (CMG) module 1400, characterized by a pressure transducer 128, is contemplated (FIG. 14), tubing of a tubing assembly bonded or welded with/to the specialty catheter, with monitoring of back pressure in a drainage conduit linking the bladder to the transducer, or sensing of bladder pressure with an adapted Foley catheter characterized by a pressure sensor carried by the catheter tip.

Woodruff et al. (U.S. Pat. No. 8,192,368) provide a specialty pressure sensing catheter characterized by a closed, pre-filled fluid (i.e., liquid) system. More particularly, a transducer assembly is permanently affixed to a urethral catheter, a predetermined previously installed charge of fluid extends from the transducer of the transducer assembly through a lumen and to the interior volume of a sensing balloon. Improved sensing accuracy and minimal set up time are stated advantages.

Finally, Burnett et al. (US 2016/0183819) provide specially equipped sensing catheters. More particularly, a dedicated pressure sensing device, such as a balloon 38 (FIG. 5A) or membrane (FIG. 5B), is supplied as part of the catheter system in addition to a retention balloon 36. The dedicated pressure sensing element is contemplated in combination with further sensing elements such as analyte and/or temperature sensors 50, 32.

In-as-much as the specialty catheters have found favor, there is a general and continuing appreciation to leverage an already deployed Foley catheter to secure pressure data. For instance, Goedje et al. (US 2012/0041334) generally disclose a pressure measuring unit for use with a urethral catheter. The unit includes a pressure sensor and essentially plumbing which permits, in the alternative, via select valving of the plumbing, either the sensing of gas pressure in a balloon via a balloon lumen, or sensing of bladder pressure via a bladder lumen. A controller, operatively linked to the pressure measuring unit, is adapted to receive pressure measurement signals from the pressure sensor and to calibrate a calibration of internal balloon pressure relative to the urine/bladder pressure.

Nishtala et al. (U.S. Pat. No. 8,337,411) disclose a variety of bypass devices, for use in combination with clamps or valves, for measuring intra-abdominal pressure (IAP) utilizing an already, as opposed to specifically deployed urethral catheter. Bypass devices are contemplated for connecting to a sampling port of a catheter system (see e.g., FIG. 1A), or to an inflation port of such system (see e.g., FIG. 31A).

Finally, Nishtala (U.S. Pat. No. 8,535,237), in keeping with his earlier work, provides a bypass device (FIG. 3) for operative union with a standard Foley catheter. The device is characterized by, among other things, a valve, a syringe with plunger, and a compression chamber, the device aiding in priming the contemplated intra-abdominal pressure monitoring system and balancing/equilibrating the system.

While device specialization has its place, it remains desirable to leverage the elegant simplicity of the standard indwelling urinary catheter in furtherance of securing urodynamic data. Moreover, stakeholders, e.g., first and foremost patients, as well as care providers, insurers, etc., desire right sizing treatments. Further still, it is believed, especially in the instant context, that, while technologic advances, whether it be more robust sensing or enhanced sensing precision via improved indwelling devices or appurtenant advanced electronics to support same, are welcome, when it comes to basic data gathering, a less-is-more approach characterized by an easy to use system or kit of few elements remains desirable and advantageous. Thus, a system, ideally enabled in a kit format, for quick, reliable, secure integration with a previously deployed indwelling urinary catheter, and further still, a related protocol for determining indwelling catheter removal conditions, is sought.

SUMMARY OF THE INVENTION

A vesical pressure measurement system and/or kit, to, among other things, implement a protocol for determining indwelling catheter removal conditions, is generally provided. One or more elements of the kit are operably combinable with a previously deployed indwelling urinary catheter. The kit includes a urodynamic data system, and a catheter balloon adaptor. The urodynamic data system is characterized by a pressure sensor for vesical pressure measurement and a processor/controller for receiving, processing and/or displaying select urodynamic patient parameters comprising sensed/monitored pressure data. The catheter balloon adaptor, for operably uniting the pressure sensor of the urodynamic data system to a balloon inflation valve of the indwelling urinary catheter, includes an adaptor valve for connection to the balloon inflation valve, and a housing. The housing includes a balloon inflation valve portion, and an adaptor valve portion, one housing portion of the housing portions being urgingly advanceable in respect of another housing portion of the housing portions in furtherance of establishing and maintaining a secure interface between the balloon inflation valve and the adaptor valve.

A diagnostic drainage catheter assembly is further contemplated. The assembly is generally characterized by an indwelling urinary catheter, an apparatus for sensing, measuring, or monitoring select patient urodynamic parameters, and an assembly for operably uniting the apparatus with a bladder anchoring balloon of the indwelling urinary catheter. The indwelling urinary catheter is characterized by a urine drainage lumen, a bladder anchoring balloon, a balloon inflation valve, and a balloon filling lumen operably linking the balloon inflation valve with the bladder anchoring balloon. The assembly for operably uniting the apparatus to/with the bladder anchoring balloon of the urinary catheter is characterized by an assembly valve for operatively linking the balloon inflation valve with the apparatus, and an assembly housing. The assembly housing includes a balloon inflation valve portion, and an assembly valve portion, the housing portions adapted so as to be urgingly drawn together in furtherance of establishing and maintaining a secure interface between the balloon inflation valve and the assembly valve.

A catheter balloon adaptor assembly is further and likewise contemplated. The assembly operably unites a urodynamic data system or the like to/with the bladder anchoring balloon of the urinary catheter. It is generally characterized by an assembly valve for operatively linking the balloon inflation valve to/with the system, and an assembly housing. The assembly housing includes a balloon inflation valve portion, and an assembly valve portion, the housing portions adapted so as to be urgingly drawn together in furtherance of establishing and maintaining a secure interface between the balloon inflation valve and the assembly valve. The adaptor assembly may further and optionally include an isolation tubing assembly, the adaptor assembly indirectly linked to the system via the tubing assembly.

Finally, a method for assessing an ability of a patient to self-void, and thus determine time of removal of an indwelling urinary catheter using the indwelling urinary catheter, is provided. The method contemplates an operative combination of an advantageous vesical pressure measurement system which is readily and reliably securable to the indwelling urinary catheter so as to sense/monitor vesical pressure via a balloon fill line of the deployed indwelling urinary catheter. The system is characterized by a pressure sensor, a processor/controller for receiving, processing and/or displaying sensed pressure from the pressure sensor, and a catheter balloon adaptor for operably uniting the pressure sensor to/with a balloon inflation valve of the indwelling urinary catheter. Pressure is sensed and monitored via the pressure sensor of the system during bladder emptying and filling events. Urine flow rates, during bladder emptying events, are ascertained. Finally, sensed/monitored pressure data in relation to ascertained urine flow rates during bladder emptying events are evaluated in furtherance of determining time of removal of the indwelling urinary catheter. More specific features and advantages obtained in view of the summarized features will become apparent with reference to the drawing figures and DETAILED DESCRIPTION OF THE INVENTION.

BRIEF DESCRIPTION OF THE DRAWINGS

All figures have been prepared, and are included to facilitate and/or enhance an understanding of the basic teachings of the contemplated embodiments, and/or the concepts underlying same and are incorporated in and constitute a part of this specification. While the drawings illustrate embodiments and context with respect thereto, and together with the description serve to explain principles of embodiments, other embodiments and many of the intended advantages of the disclosed systems, subsystems, assemblies, subassemblies, apparatus, device, mechanism, etc. will be readily appreciated as they become better understood by reference to the following detailed description and figures. It is to be noted that the elements of the drawings are not necessarily to scale relative to each other, with like reference numerals designating corresponding similar parts/structures.

FIGS. 1-9 are provided herewith wherein:

FIG. 1 depicts an indwelling urinary drainage catheter, namely, a Foley catheter;

FIG. 1A is a section of the catheter of FIG. 1, more particularly, a section about line 1A thereof;

FIG. 2 depicts preferred, non-limiting components, in operative combination, of an advantageous diagnostic drainage catheter system for use with the catheter of FIG. 1;

FIG. 3 depicts, side elevation, a contemplated assembly of the system of FIG. 2 for operatively uniting a pressure sensing subassembly to the catheter;

FIG. 4 depicts, exploded perspective view, the assembly of FIG. 3;

FIG. 5 depicts, perspective overhead view from the left, a further contemplated assembly for operatively uniting a pressure sensing subassembly to the catheter, elements thereof being see-thru to reveal underlying detail, in operative combination with a balloon inflation valve of an indwelling urinary drainage catheter;

FIG. 6 depicts, perspective overhead view from the right, a further contemplated assembly for operatively uniting a pressure sensing subassembly to the catheter, elements thereof being see-thru to reveal underlying detail, in operative combination with a balloon inflation valve of an indwelling urinary drainage catheter;

FIG. 7 depicts, axial section view, the combination of FIG. 6;

FIG. 8 depicts, perspective overhead view from the right, a first housing portion of a housing of the assembly of the combination of FIG. 6; and, FIG. 9 depicts, perspective overhead view from the left, a second housing portion of a housing of the assembly of the combination of FIG. 6.

DETAILED DESCRIPTION OF THE INVENTION

Figure 3:
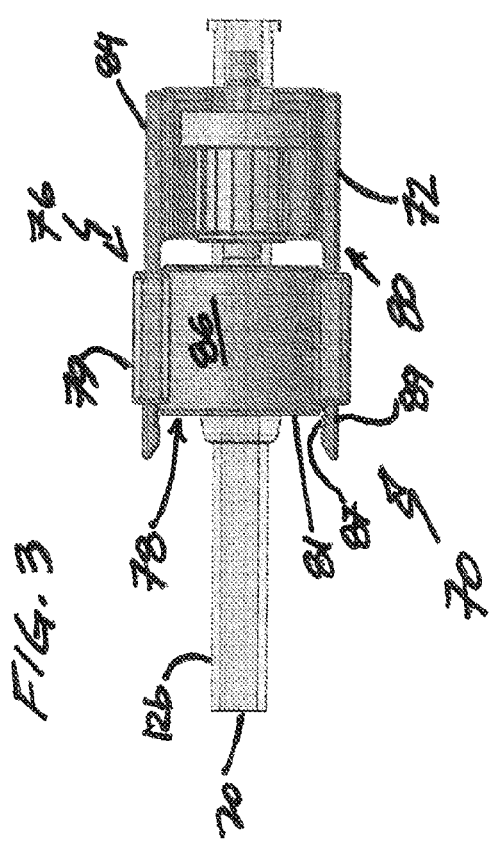

Preferred, non-limiting systems, kits, assemblies, structures and/or mechanisms relating to and enabling assessment of patient urodynamics are generally disclosed, presented and/or represented throughout the figures of the subject disclosure. An advantageous, non-limiting system is generally depicted in FIG. 2 for operative combination with the indwelling urinary catheter of FIG. 1. Several advantageous, non-limiting adaptor assemblies of the contemplated system are generally depicted in each of FIGS. 3, 5 & 6, the remaining figures directed to particulars for/of select depicted assemblies. In advance of particulars for or with regard to the instant diagnostic drainage catheter system, in all contemplated and/or disclosed forms, some preliminary observations and/or comments as to Applicant's diagnostic approach are set forth.

Advantageously, Applicant's diagnostic approach is directed to individuals (i.e., patients) that have been catheterized and are, at the time of assessment, subject of indwelling urinary catheterization. A lesser/least invasive approach is welcome and valued by all stakeholders.

Moreover, a less-is-more system or kit approach is contemplated, with a system or kit that lacks the heretofore known complexity and that is especially user friendly is likewise viewed as welcome and valued by all stakeholders. Further still, in-as-much as the scope of contemplated diagnostics may be robust/varied, an important overarching objective of the contemplated diagnostic system or kit is an informed, get-it-right-the-first-time removal of the indwelling device from the patient. Predictive protocols with regard to catheter removal are enabled and hereinafter disclosed via vesical pressure measurement and assessment while the indwelling catheter is in place, with such approach welcome and valued by all stakeholders.

Finally, an easy to use, secure linkage assembly is provided for operatively uniting the indwelling urinary catheter, via its balloon inflation valve, to/with a pressure sensing element. Notionally, a "clamp" is provided which effectively deactivates the catheter's luer-actuated value, part-and-parcel of the balloon fill line thereof, via a clamp valve of the clamp, the clamp being lockable relative to the catheter/catheter luer-actuated balloon inflation valve. Moreover, an optional valved extension assembly is provided, a first valve thereof effectively disabling the clamp valve, the second, downstream valve for operative union with a urodynamic data system input/inflow (e.g., pressure sensor). Further still, the contemplated urodynamic data system input/inflow, advantageously, but not exclusively characterized by a pressure transducer, connects to a linkage assembly valve, e.g., the clamp valve or the second valve of the valved extension assembly, so as to deactivate same, the pressure from the balloon fill line thusly directly contacting the pressure transducer in furtherance of detecting, monitoring, recording, etc. same.

With initial reference to FIGS. 1 & 2, there is generally and collectively shown elements of an advantageous diagnostic drainage catheter assembly, namely, and broadly, an indwelling urinary drainage (Foley) catheter 10 (FIG. 1) and a vesical pressure measurement system or kit 40 (FIG. 2). As will be subsequently taken up, the system of FIG. 2, or a variant thereof, via a balloon adaptor thereof, is quickly and reliably operably affixable with/to an indwelling urinary drainage catheter previously deployed for selective drainage of urine from the bladder. Advantageously, the catheter balloon catheter is easily united with the indwelling catheter; a gloved clinician can readily, swiftly and securely attached the adaptor, even with one hand in the case of translational engagement, and no uncertain terms, without resort to hardware or the like. Moreover, it is believed desirable and advantageous to establish or otherwise provide an interface that is tamper proof or at least tamper evident. While a standard 2-way Foley is shown, use of the system/kit is not so limited, with a standard 3-way Foley and alternate indwelling catheters (e.g., Duette by Poiesis Medical, Florida, USA) likewise contemplated and suitable.

System or kit 40 advantageously and desirably includes a urodynamic data system 50 characterized by a pressure sensor 52 for vesical pressure measurement during both bladder filling and emptying states, and a processor/controller 54, programmable or otherwise, for receiving, monitoring, processing, and/or displaying select urodynamic patient parameters comprising sensed/monitored pressure data, and a catheter balloon adaptor 70 for operably uniting the pressure sensor of the urodynamic data system to a balloon inflation valve of the catheter. While the system may take numerous forms, in all its forms it is contemplated to be a portable, totable, etc. system intended for multiple, and even other uses as circumstance may warrant, unlike the catheter balloon adaptor which, like the catheter itself, is a limited use item or device.

Preferably, but optionally, the system or kit further includes an isolation tubing assembly 90 interposed between balloon adaptor 70 and pressure sensor 52 as shown, and/or a fluid flow regulator (not shown) for operative combination with urine conduit 18 of catheter 10 (FIG. 1/1A). Advantageously, but not necessarily, the isolation tubing assembly may be integral to the catheter balloon adaptor (i.e., a built-in feature of the adaptor assembly). The fluid flow regulator may take the form of a Cunningham clamp or a Flip Flo® catheter valve from Bard Medical, Covington, Ga., USA, however, it is believed desirable to provide a selectively actuated valve for operative linkage to/with the urodynamic data system.

Preferably, but optionally, urodynamic data system 50 is or may be characterized by, among other things as will be latter taken up, an output device 56 (e.g., a phone, tablet, PC, etc.) operably linkable to processor 54, a database 58 accessible by processor 54, a weighing scale 60 (see e.g., Applicant's EasyFlo Stand-alone Uroflow system) operably linkable to or adapted for integration with processor/controller 54 for determining a mass of collected fluid discharging from the urine conduit of the Foley catheter in furtherance of determining a fluid flow rate, and/or electromyography (EMG) electrodes 62 operably linkable to processor/controller 54 in furtherance of ascertaining patient abdominal and/or perianal activity.

Figure 5:
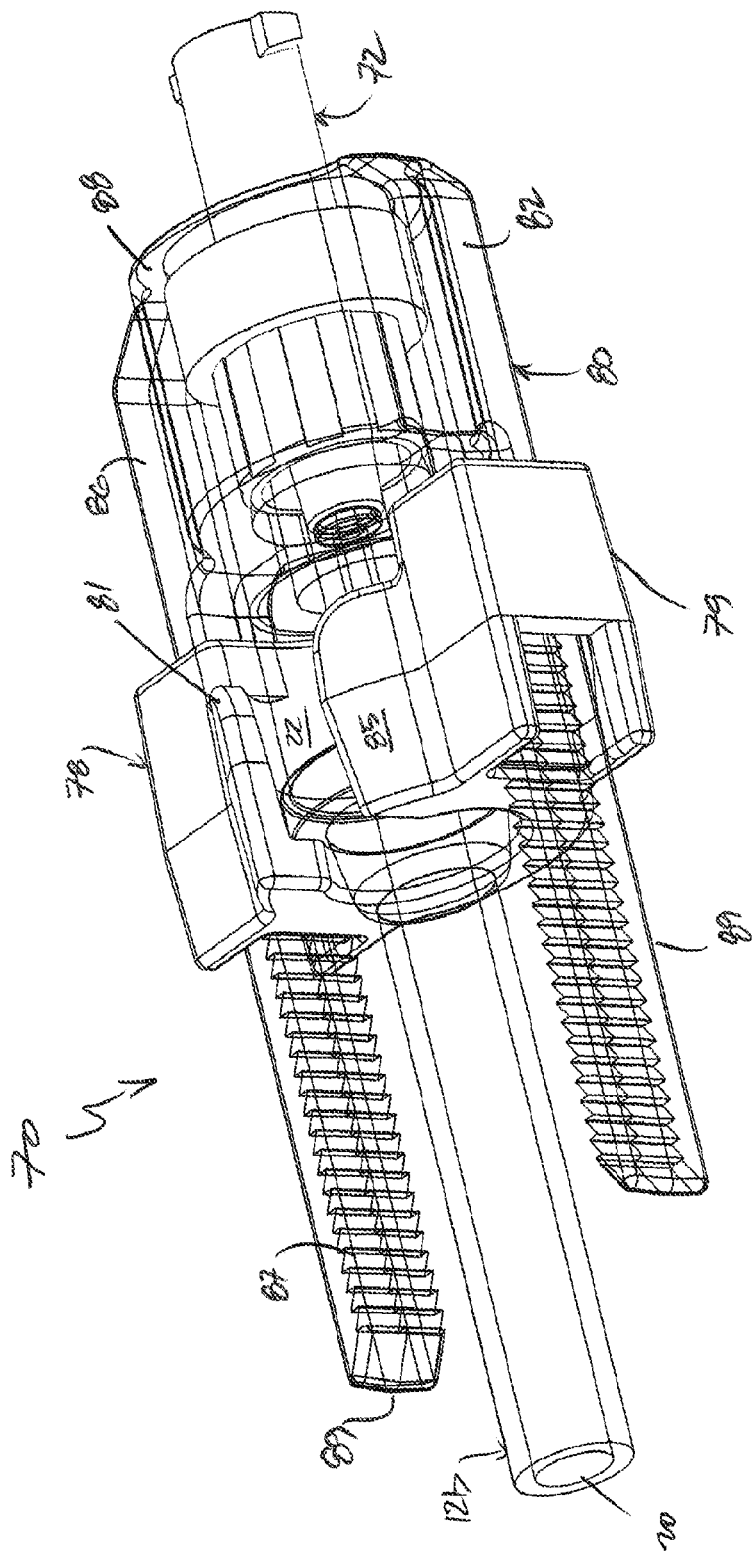
Figure 7:
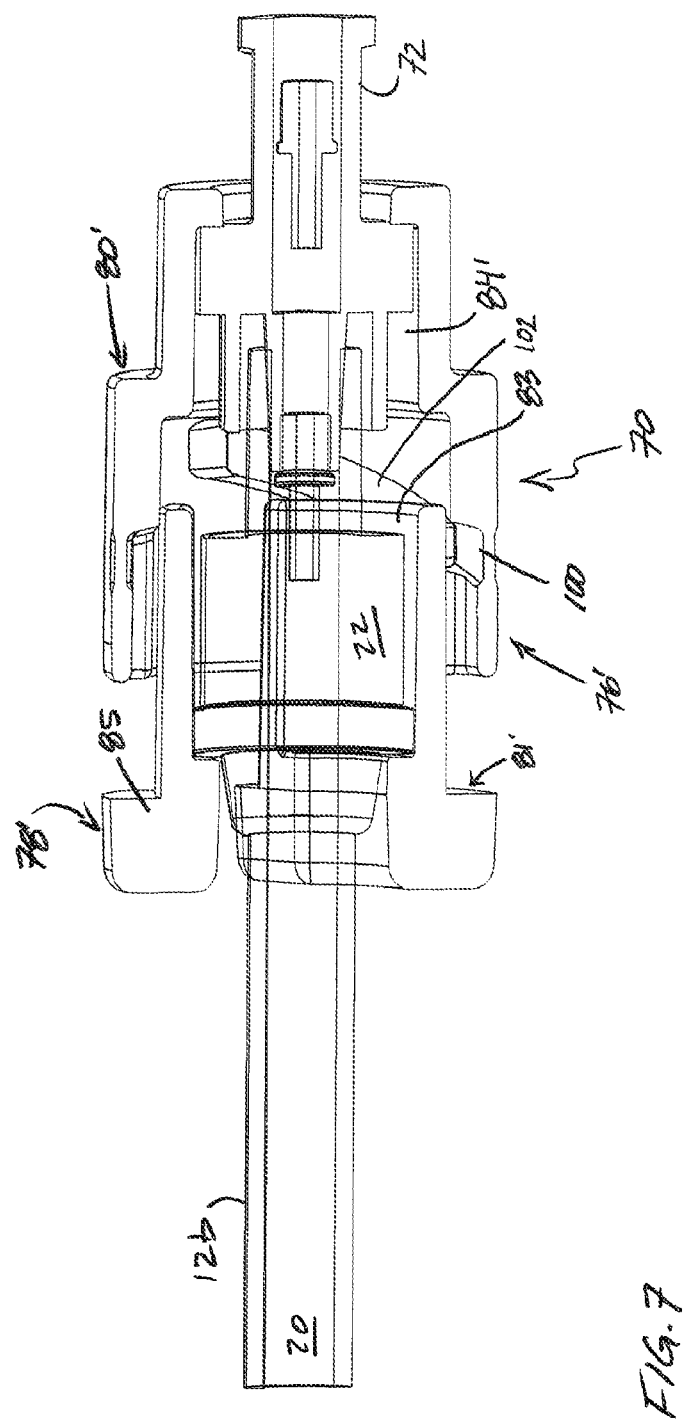

With particular reference now to the catheter balloon adaptors of each of FIGS. 3 & 5, and with passing reference to the alternate adaptor embodiment of FIG. 7, adaptor or assembly 70 advantageously includes an adaptor valve 72 for operatively linking balloon inflation valve 22 with an apparatus for sensing, measuring, or monitoring select urodynamic parameters (e.g., urodynamic data system 50), and a housing 76. Adaptor housing 76 includes a balloon inflation valve portion 78, and an adaptor valve portion 80, the portions operably uniteable (e.g., selectively affixable) in furtherance of establishing and maintaining a secure interface between balloon inflation valve 22 and adaptor valve 72. More particularly, one housing portion of the housing portions is urgingly advanceable in respect of another housing portion in furtherance of establishing a quick, secure union of the adaptor or adaptor assembly to/with the catheter. As will be later discussed, the housing portions are adapted to be urgingly drawn together, e.g., via translation (FIG. 3 or FIG. 5) or rotation (FIG. 7) of one housing element relative to another.

Adaptor valve 72 of balloon adaptor 70 mates with catheter inflation valve 22, and advantageously comprises a luer activated valve. The adaptor valve is characterized by a stem which deactivates the luer-activated valve of the catheter's balloon fill line. For example, and as shown, a preferable adaptor valve is a female to male luer (Qosina PN QOS5401036SN).

Housing 76 of balloon adaptor 70 is advantageously, but not necessarily a two-part housing as shown. Via after described preferable non-limiting structures, the housing may be assembleable about a valved union between, among and for the catheter and an apparatus for sensing, measuring, or monitoring select urodynamic parameters. Contrariwise, and advantageously, the adaptor assembly is provided in a pre-loaded state (i.e., the housing portions are operatively linked, via a cooperative interface, in a spaced apart condition, the assembly being tensioningly received or manipulated about the catheter inflation valve, with the adaptor valve housing portion translatingly urged into operative engagement therewith subsequent to urgingly advancing the adaptor valve housing portion towards inflation valve housing portion).

Figure 4:
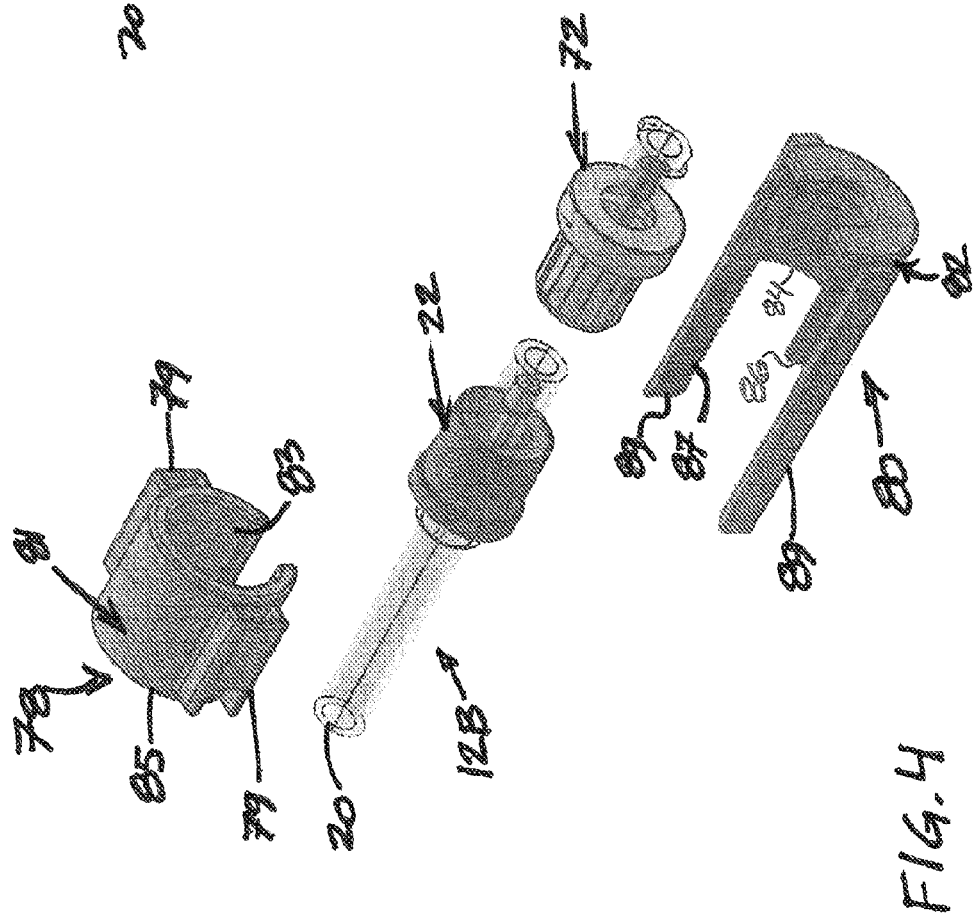

Balloon inflation valve portion 78 of housing 76 is configured to circumscribe balloon inflation valve 22. This housing portion (i.e., housing body portion) is generally characterized as a cuff or sleeve comprised of a circumferential or partially circumferential sidewall 81 which at least partially circumscribes the balloon inflation valve. The sidewall includes interior 83 and exterior 85 surfaces (FIG. 4). Notionally, while this housing portion may function as a spring clip in furtherance of ready securement about the balloon inflation valve, it is advantageously received about the inflation segment body of the catheter via a sidewall groove, with the so positioned housing portion slide over the inflation valve.

Interior surface 83 of sidewall or partial sidewall 81 is advantageously adapted (e.g., contoured) to seat or at least cooperatively receive a portion of the balloon inflation valve. Exterior surface 85 of sidewall or partial sidewall 81 is adapted to cooperatively engage, for example and advantageously, urgingly engage with and irreversibly receive adaptor valve portion 72 of housing 70. More particularly, balloon inflation valve housing body portion 78 is advantageously equipped with a guide or retainer for receipt of a portion or portions of the adaptor valve housing body portion 80, for example, opposingly paired guides 79 extend from exterior surface 85 thereof as shown. The guide or retainer advantageously functions to aid in quick reliable housing assembly (i.e., registration of the housing portions) and to secure the housing portions about an operative union of the adaptor valve and balloon inflation valve to thus fortify that interface, namely, a zip or ratcheted interface.

Adaptor valve portion 80 of housing 76 generally circumscribes adaptor valve 72. This housing portion (i.e., housing body portion) is generally characterized as a cuff or sleeve having a circumferential or partially circumferential sidewall 82, which at least partially circumscribes adaptor valve 72, and an end wall 88 through which a portion of adaptor valve 72 is passable. Sidewall 82 includes interior 84 and exterior 86 surfaces (FIG. 4). Advantageously, the adaptor valve housing portion and the adaptor valve are provided in the form of an integrated subassembly (FIG. 5).

Interior surface 84 of sidewall or partial sidewall 82 is advantageously adapted (e.g., contoured) to seat or at least cooperatively receive a portion of adaptor valve 72. Exterior surface 86 of sidewall or partial sidewall 82 is adapted to cooperatively engage, for example and advantageously, urgingly unite with balloon inflation valve portion 78 of housing 76. More particularly, adaptor valve housing body portion 80 is advantageously adapted to include or carry a depending element or elements receivable in the guide or retainer of the balloon inflation valve housing body portion, for example, opposingly paired arms 89 as shown. In furtherance of establishing a secure translating engagement for, between and among the housing portions, either or both of the arms 89 and retainers 79 of their respective housing portions 80, 78 may be suitable adapted to form an interference fit, for example, a portion of mating surfaces of the arms and retainers includes a toothed surface, see e.g., toothed surface 87 of arm 89 of assembly valve housing body portion 80. Again, as was noting in passing, such interface, especially in a preloaded assembly configuration, provides a supremely easy to affix and adjust (snug) the assembly in relation to the catheter balloon valve, and, with the noted structures, establish an interface one that is not readily undone or reversed.

Figure 6:
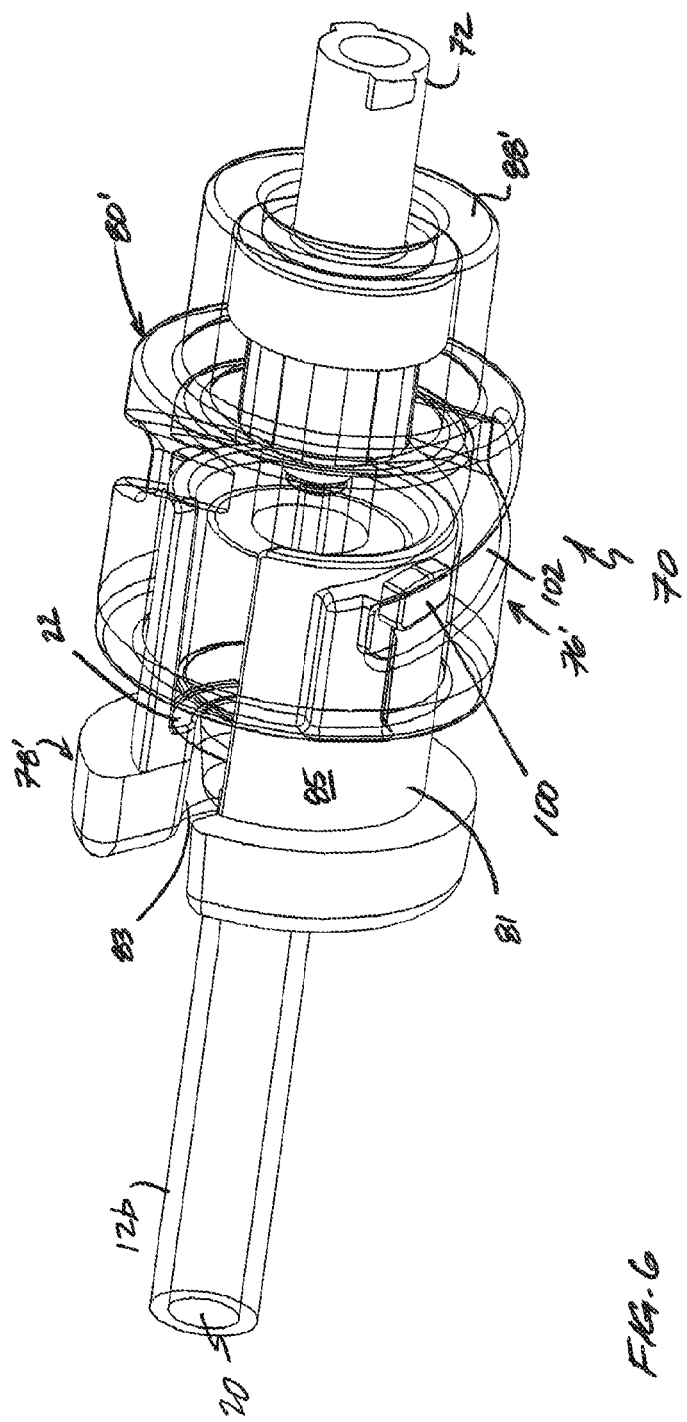
Figure 8:
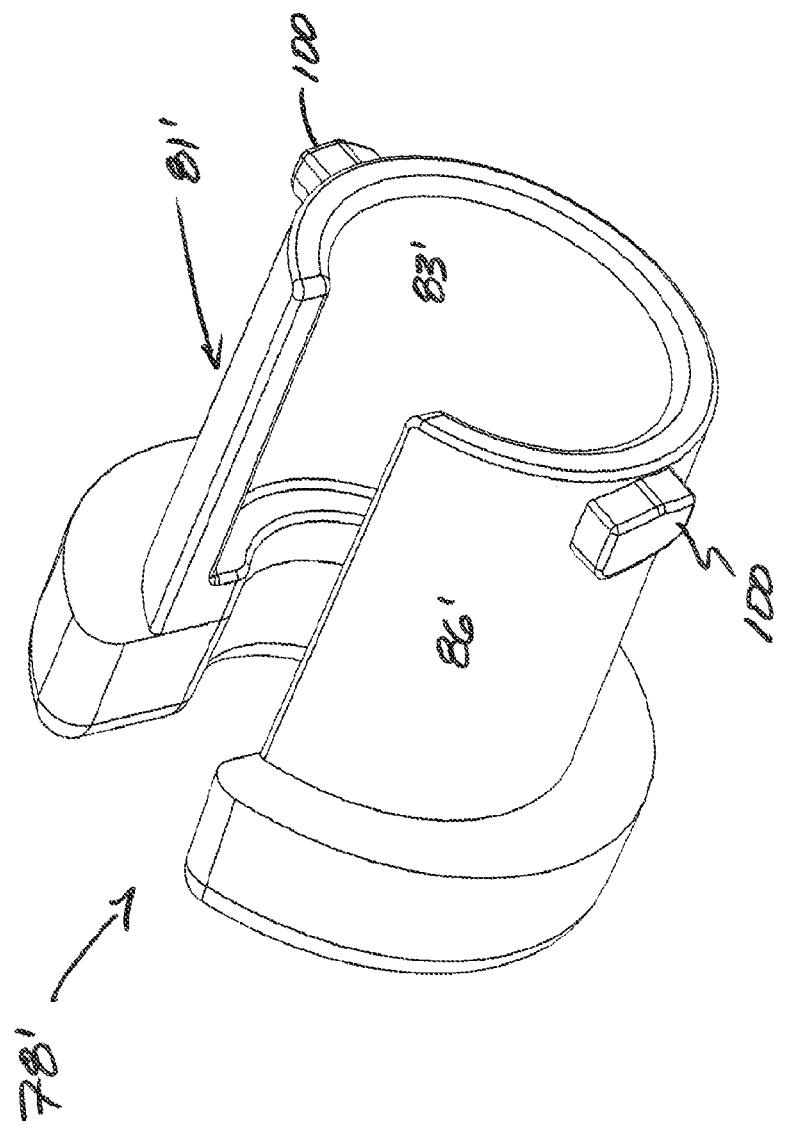
Figure 9:
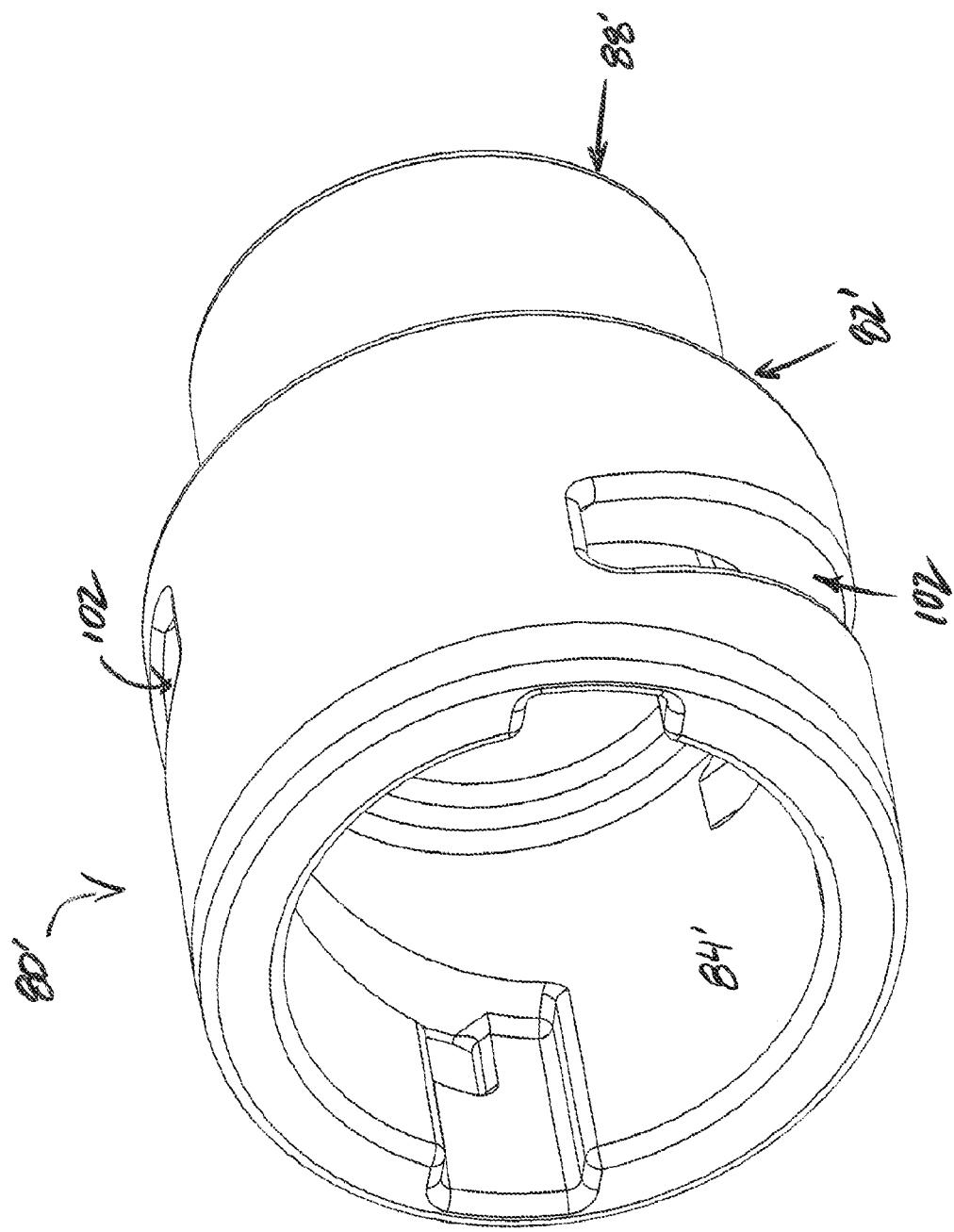

With reference now to the catheter adaptor assembly of FIG. 6 and the particulars thereof depicted in FIGS. 7-9, adaptor or assembly 70' advantageously includes an adaptor valve 72' for operatively linking balloon inflation valve 22 with an apparatus for sensing, measuring, or monitoring select urodynamic parameters (e.g., urodynamic data system 50 (FIG. 2)), and a housing 76'. Adaptor housing 76' includes a balloon inflation valve portion 78' (FIG. 8), and an adaptor valve portion 80' (FIG. 9), one housing portion of the housing portions being urgingly advanceable in respect of another housing portion in furtherance of establishing and maintaining a secure interface between balloon inflation valve 22 and adaptor valve 72'(i.e., establishing a quick, secure union of the adaptor or adaptor assembly to/with the catheter). As will be subsequently discussed, the housing portions are adapted to be urgingly drawn together via rotation of one housing element relative to another.

As early described, balloon inflation valve portion 78' of housing 76' (FIG. 8) is configured to circumscribe balloon inflation valve 22. This housing portion (i.e., housing body portion) is generally characterized as a cuff or sleeve comprised of a circumferential or partially circumferential sidewall 81' which at least partially circumscribes the balloon inflation valve. The sidewall includes interior 83' and exterior 85' surfaces. Notionally, while this housing portion may function as a spring clip in furtherance of ready securement about the balloon inflation valve, it is advantageously received about the inflation segment body of the catheter via a sidewall groove, with the so positioned housing portion slide over the inflation valve.

Interior surface 83' of sidewall or partial sidewall 81' is advantageously adapted (e.g., contoured) to seat or at least cooperatively receive a portion of the balloon inflation valve. Exterior surface 85' of sidewall or partial sidewall 81' is adapted to cooperatively engage, for example and advantageously, urgingly engage adaptor valve portion 72' of housing 70'. More particularly, balloon inflation valve housing body portion 78 is advantageously equipped with a key 100 (e.g., opposing keys as shown) which is operatively received by a portion of the adaptor valve housing portion. The key advantageously functions to aid in quick reliable housing assembly (i.e., registration of the housing portions) and to secure the housing portions about an operative union of the adaptor valve and balloon inflation valve to thus fortify that interface via a rotational urged engagement for, between and among the housing portions.

Adaptor valve portion 80' of housing 76' generally circumscribes adaptor valve 72. This housing portion (i.e., housing body portion) is generally characterized as a cuff or sleeve having a circumferential sidewall 82', which circumscribes adaptor valve 72, and an end wall 88' through which a portion of adaptor valve 72 is passable. Sidewall 82' includes an interior surface 84' having a portion adapted, for example, via inclusion of a relief area or segment, for initial receipt of key 100 of housing portion 78. Sidewall 82' includes a keyway 102 (e.g., opposing keyways as shown) in the form of a slot or the like having an end that terminates at the relief area of the interior surface of the sidewall. Advantageously, the keyway is off-set from vertical, integration of the key of the inflation valve housing body portion with the keyway of the adaptor valve housing portion via a twisting motion resulting in a rotatingly urged engagement of, for and between the housing portions, and thus, a fortified union between the housed valves.

With renewed reference to the system of FIG. 2, it is believed both advantageous and desirable to isolate the fluid/liquid of the balloon (i.e., balloon environment) from the pressure sensing element (i.e., avoid direct contact/engagement of the sensor/sensed media). Toward that end, the contemplated system further, but not necessarily, includes isolation tubing assembly or extension 90 which operatively links the catheter, via the housing (more particularly, the adaptor valve thereof), to and with the pressure sensing element.

Isolation tubing extension 90 is characterized by a male luer 94 (e.g., a Qosina 71627 luer) on the catheter end of the conduit (i.e., tube 90), more particularly, the luer is carried upon a length (e.g., 4 inch long length) of air-tight tubing (e.g., Qosina T2005 tubing) which in turn is connected to a valved female luer lock connector 96 (e.g., Qosina QOS5401036SN luer lock) for operative receipt of pressure sensor 52. The catheter end valve essentially disables the catheter balloon adaptor valve upon engagement therewith. A contemplated alternative, advantageous approach includes integrating the isolation tubing extension to the housing or a portion thereof, thus rendering the catheter end valve of the extension assembly a surplus.

The benefit of the isolation tubing is that it can be utilized to isolate the liquid in the balloon from the pressure sensing element, allowing the pressure sensing element to be uncontaminated by the liquid. Without the isolation tubing, the sensing element of a pressure transducer comes in direct contact with the liquid in the balloon. The isolation tubing is open at one end, and valved at the other end. It contains an initial volume or fluid charge (e.g. air) which acts as a buffer between the liquid in the balloon and the pressure transducer.

With continued reference to FIG. 2, pressure sensor 52 is advantageously, but not exclusively provided in the form of a chip based sensor, the sensor having an integral luer fitting for ready union with either of a free end of the isolation tubing extension or assembly (FIG. 2), or the adaptor valve. A preferred embodiment of the pressure sensor comprises a single use pressure sensor, polycarbonate, with luer (sterile), PN PRESS-S-000 from PendoTECH, Princeton, N.J., USA.

Processor/controller 54 of urodynamic data system 50 functions advantageously to, for example, at least monitor/monitor-display, and transmit sensed pressure from pressure sensor 52. A preferred embodiment of the processor/controller comprises a PressureMAT™ Sensor Monitor from PendoTECH, the unit further providing a signaling/alarm functionality. Moreover, inclusion of one or more data ports in/for the processor/controller is believed desirable and advantageous, with attendant data acquisition and/or management software likewise desirable. Towards that end, a preferred processor is further characterized by PressureMAT Data Acquisition Software from PendoTECH. As will subsequently presented, processing further contemplates comparison of received urodynamic patient parameter values as a function of time and/or select comparison with a database of urodynamic parameter values in furtherance establishing and/or utilizing a normative database which describes, for instance, the relationship between vesical pressure at different states and voiding symptoms.

While there are potential disadvantages of measuring pressure through a balloon line, e.g., adaptation of the balloon inflation valve for union to a pressure sensor arguably increases the incidence of inadvertent balloon leakage, and measurements premised upon a less than optimally positioned anchor balloon, there are greater advantages to such approach. For instance, the balloon chamber (i.e., volume delimited by the balloon) is completely isolated from the bladder, therefore there is no risk that the pressure measurement will result in contaminants traveling through the lumen of the line to/into the bladder of a patient. Moreover, the balloon line can be filled with a fixed column of fluid (i.e., liquid or gas (e.g., water or air)), resulting in improved measurement accuracy by the pressure transducer or the like. Further still, the measurement of vesical pressure can be made without concern for the amount of urine in the bladder, and the measurement of pressure does not implicate use of the urine drainage line, thusly, that functionality of/for the indwelling urinary drainage catheter is preserved.

The contemplated bladder vesical pressure determination can be implemented with either of a single balloon or two balloon urinary drainage catheter. Moreover, implementation is contemplated with either of indwelling urinary drainage catheters (i.e. Foley style), or intermittent urinary drainage catheters.

In the single balloon embodiment, the balloon is filled through a valve that allows the connection to a pressure transducer. A pressure transducer can be utilized that allows for a fixed column (i.e., volume) of fluid (i.e., liquid or gas) to be introduced into the line. Alternatively, a traditional syringe can be used to fill the balloon line. Once the balloon is filled, vesical pressure can be monitored continuously or selectively, without concern about the amount of urine in the bladder and without affecting the urine drainage properties/functionality of the catheter.

In the two balloon embodiment, vesical pressure can be measured in a secondary balloon that is not the bladder retaining anchor (i.e., the distal balloon). The primary retaining balloon can be traditionally filled (i.e., using a one-way valve) and placed (i.e., at the bladder neck). A second balloon, which may simply act as a vesical pressure sensor or also act, for example, to prevent the bladder wall apex from resting on the top of the catheter, would be filled with a column of liquid or gas (i.e., volume of fluid) and vesical pressure continuously, intermittently and/or selectively monitored.

There are two main advantages to a two balloon embodiment: (a) the measurement of vesical pressure does not change the design of the one-way valve of the retaining balloon, mitigating any additional risk of retaining balloon deflation; and, (b) the placement of the balloon indicating vesical pressure can be placed in an optimal location to more accurately reflect vesical pressure. For example, if the second balloon is placed above the retaining balloon, it can be assured of not being in contact with the bladder neck. It should be noted that these two advantages may also be realized with an intermittent catheter with a single balloon design that does not utilizing a retaining balloon. The single balloon could be placed optimally, similar to the placement methodology with traditional urodynamic measurement catheters.

In advance of particulars relating to or for select contemplated operational sequences, diagnostic methods and/or clinical protocols enabled by aforementioned systems/assemblies (e.g., real time sensing/monitoring of vesical pressure during catheter indwell), some initial comments are warranted.

Catheter management leveraging vesical pressure measurement via an indwelling urinary drainage catheter is compelling. Real time monitoring of vesical pressure, urine discharge rates, abdominal EMG and patient bladder sensation are readily ascertainable. Indwelling urinary catheter removal is predicated upon establishment of a vesical pressure adequate for the given patient to void. Moreover, via an automated safety drainage clamp/valve system, a patient can self-actuate to void in a by-pass mode, a clinician can program for select automated drainage to prevent an overfill condition, and, via an override, select automated relief drainage is possible. Exercising of the bladder reduces the length of catheter need, with an automated determination of catheter removal via targeted vesical pressure monitoring, including establishment of a predictive removal model achievable. Finally, the contemplated approach has utility for baseline measurement in relation to surgery candidates (i.e., pre-surgical benchmarking).

Beyond the threshold operation of sensing and measuring vesical pressure during catheter indwell using a balloon fill line thereof, several advantageous, non-limiting operations or operational sequences are illustratively noted. For example, a first operational sequence contemplates obtaining a baseline value of vesical pressure at the time of catheter deployment and upon confirmation that the patient is in retention. Continuous or periodic measurements of vesical pressure via the previously placed catheter are thereafter obtained, with a formulaic identification/prediction (e.g., via an improvement in vesical pressure pattern identification) that the catheter can be removed, achieved, with successful voiding by the patient likely resulting.

In a further second contemplated operational sequence, vesical pressure at different states is compared/comparable to a normative database which describes the relationship between vesical pressure at different states and voiding symptoms.

In a further third contemplated operational sequence, vesical pressure data informs a determination that a patient has vesical pressure adequate to successfully void absent a bladder outlet obstruction. If a patient could not adequately void after catheter removal, bladder outlet obstruction could be diagnosed and in a male patient, a temporary prostate stent (e.g., The Spanner® from SRS Medical Systems, LLC, MA, USA) could be implanted. The measurement of vesical pressure could predict whether a patient could successfully void with a temporary prostate stent.

In a further fourth contemplated operational sequence, a pinch valve or clamp is applied to the indwelling urinary catheter to allow the bladder to naturally fill without draining through the catheter urine ports. In this manner, vesical pressure can be measured while the patient's bladder is naturally filling. When the clamp is removed and the patient voids, vesical pressure can be measured during the void. These data can be formulaically analyzed to predict if the catheter can be removed and will likely result in successful voiding by the patient.

In a further fifth contemplated operational sequence, measurements of vesical pressure are made and formulaically analyzed to estimate detrusor pressure. Detrusor pressure is defined as the abdominal pressure minus the vesical pressure (i.e., abdominal pressure is characterized by a combination of detrusor pressure and vesical pressure). By monitoring the vesical pressure over time while the patient is at rest and/or when the patient is asked to perform physical activities, e.g., a Valsalva Maneuver, predictive models are enabled in furtherance of predicting the contribution of detrusor pressure to the measured vesical pressure at different times.

In a further sixth contemplated operational sequence, simultaneous measures of abdominal activity using surface EMG electrodes placed on the abdomen are sought. Data from the electrodes provide insight into abdominal pressure, and thus further improve the prediction of detrusor pressure contribution to the measured vesical pressure.

In a further seventh contemplated operational sequence, simultaneous measures of perianal activity using surface EMG electrodes placed on the perineum are sought. Data from the electrodes provide insight into sphincter-detrusor dyssynergia and may be utilized to further predict whether the patient will be able to void without the catheter.

In a further eighth contemplated operational sequence, a granular predictive model for determining indwelling urinary catheter removal is realized. For instance, rather than predicting that the catheter should or should not be removed, an advantageous embodiment of the contemplated system could predict the likelihood, e.g., on a percentage basis, that the patient will be able to void successfully. For example, an analysis of the available data (e.g., combination of collected and reference data) might permit predictive determination that the patient is 82% likely to be able to successful void. Alternatively, an analysis of the available data might permit a further predictive determination as to the likelihood that the patient could void to a pre-specified, post-void residual, or the likelihood that the patient would go into acute urinary retention.

In a further ninth contemplated operational sequence, the predictive model might be supplemented with data beyond the vesical pressure measurements and the EMG measurements. For instance, patient demographics (e.g., age, gender), patient health history, and patient current symptoms data could be incorporated into the predictive model.

In addition to the aforementioned illustrative operational approaches, a desirable, advantageous, robust and non-limiting clinical protocol, in relation to an indwelling catheter patient passing urine from their bladder (continuously) to a collection receptacle, is provided, and contemplates:

1. Attaching an adapter of a urodynamic assessment assembly/kit to the balloon inflation port of an indwelling urinary (e.g., Foley) catheter in furtherance of operatively equipping the balloon line with a pressure sensing element such as a pressure transducer.
2. Optionally adding an isolation tubing extension to the adaptor to isolate the balloon fluid from the pressure sensing element.
3. Securing the pressure transducer to the adapter or tubing extension, e.g., using a mating luer connection.
4. Operatively linking the pressure transducer to a data recording/processing unit or the like.
5. Optionally placing a urine collection receptacle on a weighing scale.
6. Using the recording/processing unit to "zero" the vesical pressure channel and an optional urine mass/volume channel so as to establish a baseline vesical pressure and mass of the empty urine drainage receptacle respectively.
7. Ceasing urine egress from the bladder via the urine line of the indwelling urinary catheter via actuation of a clamp or valve operatively linked thereto.
8. Selectively measuring (e.g., continuous, semi continuous or periodic) vesical pressure as the bladder is filling.
9. Optionally displaying vesical pressure data, stored or otherwise, via a display/output device of or associated with the data recording/processing unit in real-time.
10. Optionally placing an EMG electrode on the abdomen to measure abdominal muscle activity, e.g., continuous monitoring during bladder filling and emptying, acquired data used in quantify the abdominal pressure impact on vesical pressure and to ascertain detrusor pressure.
11. Optionally logging of the patient's bladder filling sensation metrics as the patient's bladder is filling, e.g., "first sensation of bladder filling" and "first desire void," with these events marked simultaneous to other collected data (i.e., correlated to/with).
12. Opening a urine drain line when the patient's bladder is full and s/he has a strong desire to void, e.g., clamp removal or valve opening, so as to allow urine in the bladder to drain into the drainage bag, vesical pressure, abdominal EMG activity, urine flow rate and total voided volume thusly ascertained.
13. Analyzing data to determine the status of the patient's bladder function and to determine whether the catheter should be removed, such analysis advantageously automated part-and-parcel of a series of targeted parameters during bladder cycling so as to determine optimal care pathways.

Advanced diagnostic information may be suitably obtained by customizing the manner in which the urine drain line is clamped and released. As per the above, the line is either closed, during bladder filling, or opened, during bladder emptying. An alternative approach would be to use a valve that was closed during filling but during emptying, its effective resistance could be variable so as to simulate the effect of urethral resistance, such as that found in patients with Benign Prostate Hyperplasia. By adjusting the outlet resistance, the vesical pressure-outlet resistance-urine flow rate relationships could be established to further determine the optimal care pathway.

Commonly, there is a concern that patients who do not have sensation or are cognitively impaired will not open the drain line and empty the bladder. A such, this could result in overfilling of the bladder, and to reflux of urine into the kidneys. A selectively actuatable valve may be utilized, the valve selectively actuatable, i.e., opened, based on either a select time interval (e.g., every 4 hours), or based on other conditions, e.g., such as vesical pressure), or a combination of several conditions.

As to the urine weighing scale, it may be readily adapted to include an alarm/alarm mode to indicate when the valve is opened and the urine is draining, or if no urine or a low volume of urine empties into the drainage bag. These conditions could be caused by a blockage in the catheter, or by a lack of urine production by the patient, both of which are clinical events potentially requiring intervention.

What has been described and depicted herein are preferred, non-limiting embodiments of Applicant's subject matter, along with some application contexts. Since the elements of the system and/or structures of the assemblies, subassemblies, and/or mechanisms disclosed herein may be embodied in other specific forms without departing from the spirit or general characteristics thereof, some of which forms have been indicated, the embodiments described and depicted herein/with are to be considered in all respects illustrative and not restrictive. Moreover, while nominal operational steps or sequences and/or a protocol have been set forth, and to some degree alternate work pieces and systems, assemblies, etc. with regard thereto referenced, contemplated sequences/protocols are not so limited. Accordingly, the scope of the subject invention is as defined in the language of the appended claims, and includes not insubstantial equivalents thereto.

That which is claimed:

1. A vesical pressure measurement system to implement a protocol for determining indwelling catheter removal conditions, one or more elements of the system operably combinable with a previously deployed indwelling urinary catheter, the system comprising:
   a. urodynamic data system characterized by a pressure sensor for vesical pressure measurement during either of bladder filling or emptying events, and a processor/controller for receiving, processing and/or displaying select urodynamic patient parameters comprising sensed/monitored pressure data;
   b. a catheter balloon adaptor for operably uniting said pressure sensor of said urodynamic data system to a balloon inflation valve of the indwelling urinary catheter, said catheter balloon adaptor comprising an adaptor valve with a deactivation stem for connection to the balloon inflation valve, and a housing, said housing comprising a balloon inflation valve portion and an adaptor valve portion, one housing portion of said housing portions being urgingly advanceable in respect of another housing portion of the housing portions, said housing portions of said catheter balloon adaptor being irreversibly interlocking portions in furtherance of establishing and maintaining a secure operable interface between said balloon inflation valve and said adaptor valve.

2. The system of claim 1 further comprising a fluid flow regulator for operative combination with a urine conduit of the catheter.

3. The system of claim 2 wherein said fluid flow regulator comprises a clamp.

4. The system of claim 2 wherein said fluid flow regulator comprises a valve for select actuation by said processor/controller of said urodynamic data system in response to processed urodynamic patient parameters.

5. The system of claim 1 wherein said catheter balloon adaptor further comprises an isolation tubing assembly, said isolation tubing assembly extending from said adaptor valve for union with said pressure sensor of said urodynamic data system.

6. The system of claim 1 further comprising an isolation tubing assembly, said isolation tubing assembly extending between said catheter balloon adaptor and said pressure sensor of said urodynamic data system.

7. The system of claim 6 wherein said isolation tubing is integral to said catheter balloon adaptor.

8. The system of claim 1 wherein said housing portions of said catheter balloon adaptor are urgingly advanceable one towards the other via translation.

9. The system of claim 1 wherein said housing portions of said catheter balloon adaptor are urgingly advanceable one towards the other via rotation.

10. The system of claim 1 wherein said adaptor valve house portion is urgingly advanceable relative to said balloon inflation valve housing portion.

11. The system of claim 1 provided as a kit.

12. The system of claim 1 wherein said balloon inflation valve and said adaptor valve portions of said housing are pre-loaded.

13. The system of claim 1 wherein said balloon inflation valve and said adaptor valve portions of said housing are joined.

14. The system of claim 1 wherein said balloon inflation valve and said adaptor valve portions of said housing are joinable.

15. The system of claim 1 wherein said urodynamic data system is further characterized by an output device operably linkable to said processor/controller.

16. The system of claim 15 wherein said output device comprises a phone.

17. The system of claim 15 wherein said output device comprises a tablet.

18. The system of claim 15 wherein said output device comprises a personal computer.

19. The system of claim 15 wherein said output device comprises a lap top computer.

20. The system of claim 1 wherein said urodynamic data system is further characterized by a database accessible by said processor/controller.

21. The system of claim 1 further comprising electromyography electrodes operably linkable to said processor/controller in furtherance of ascertaining patient abdominal and/or perianal activity.

22. A vesical pressure measurement system to implement a protocol for determining indwelling catheter removal conditions, one or more elements of the system operably combinable with a previously deployed indwelling urinary catheter, the system comprising:
 a. urodynamic data system characterized by a pressure sensor for vesical pressure measurement during either of bladder filling or emptying events, and a processor/controller for receiving, processing and/or displaying select urodynamic patient parameters comprising sensed/monitored pressure data;
 b. a catheter balloon adaptor for operably uniting said pressure sensor of said urodynamic data system to a balloon inflation valve of the indwelling urinary catheter, said catheter balloon adaptor comprising an adaptor valve with a deactivation stem for connection to the balloon inflation valve, and a housing, said housing comprising a balloon inflation valve portion and an adaptor valve portion, one housing portion of said housing portions being urgingly advanceable in respect of another housing portion of the housing portions in furtherance of establishing and maintaining a secure operable interface between said balloon inflation valve and said adaptor valve; and,
 c. a weighing scale operably linkable to said processor/controller for determining a mass of collected fluid discharging from the urine conduit of the catheter in furtherance of determining a fluid flow rate.

23. A vesical pressure measurement system to implement a protocol for determining indwelling catheter removal conditions, one or more elements of the system operably combinable with a previously deployed indwelling urinary catheter, the system comprising:
 a. urodynamic data system characterized by a pressure sensor for vesical pressure measurement during either of bladder filling or emptying events, and a processor/controller for receiving, processing and/or displaying select urodynamic patient parameters comprising sensed/monitored pressure data;
 b. a catheter balloon adaptor for operably uniting said pressure sensor of said urodynamic data system to a balloon inflation valve of the indwelling urinary catheter, said catheter balloon adaptor comprising an adaptor valve with a deactivation stem for connection to the balloon inflation valve, and a housing, said housing comprising a balloon inflation valve portion and an adaptor valve portion, one housing portion of said housing portions being urgingly advanceable in respect of another housing portion of the housing portions in furtherance of establishing and maintaining a secure operable interface between said balloon inflation valve and said adaptor valve; and,
 c. electromyography electrodes operably linkable to said processor/controller in furtherance of ascertaining patient abdominal and/or perianal activity.

24. A diagnostic drainage catheter assembly comprising:
 a. a urinary catheter characterized by a urine drainage lumen, a bladder anchoring balloon, a balloon inflation valve, and a balloon filling lumen operably linking said balloon inflation valve with said bladder anchoring balloon;
 b. an apparatus for sensing, measuring, or monitoring select urodynamic parameters; and,
 c. an assembly for operably uniting said apparatus with said bladder anchoring balloon of said urinary catheter, said assembly characterized by an assembly valve for operatively linking said balloon inflation valve with said apparatus, and an assembly housing, said assembly housing comprising a balloon inflation valve portion and an assembly valve portion, said housing portions adapted so as to be urgingly drawn together, said balloon inflation valve portion of said assembly housing including paired retainers, said assembly valve portion of said assembly housing including paired arms extending therefrom, said paired arms affixably received by said paired retainers in furtherance of establishing and maintaining a secure interface between said balloon inflation valve and said assembly valve.

25. The diagnostic drainage catheter assembly of claim 24 further comprising an isolation tubing assembly, said isolation tubing assembly extending between said assembly valve and said apparatus.

26. The diagnostic drainage catheter assembly of claim 24 wherein said apparatus comprises a pressure sensor.

27. The diagnostic drainage catheter assembly of claim 24 wherein said apparatus comprises a pressure sensor and a pressure sensor monitor operatively linked thereto.

28. The diagnostic drainage catheter assembly of claim 24 wherein said apparatus comprises a urodynamic data system.

29. A method for assessing an ability to self-void and thus determine time of removal of an indwelling urinary catheter using the indwelling urinary catheter, in operative combination with a vesical pressure measurement system, the method comprising:
   a. providing a vesical pressure measurement system characterized by a pressure sensor, a processor/controller for receiving, processing and/or displaying sensed pressure from said pressure sensor, and a catheter balloon adaptor for operably uniting said pressure sensor to/with a balloon inflation valve of the indwelling urinary catheter;
   b. sensing and monitoring pressure via said pressure sensor during bladder emptying and filling events;
   c. ascertaining urine flow rates during bladder emptying events; and,
   d. evaluating sensed/monitored pressure data in relation to ascertained urine flow rates during bladder emptying events in furtherance of determining time of removal of the indwelling urinary catheter.

30. The method of claim 29 further comprising obtaining a baseline value of vesical pressure post indwelling urinary catheter deployment and upon confirmation of a urine retention condition.

31. The method of claim 29 further comprising comparing sensed/monitored pressure data to a normative database which describes relationships between vesical pressure and voiding symptoms.

32. The method of claim 29 further comprising acquiring measurements of vesical pressure in furtherance of estimating detrusor pressure and determining same.

33. The method of claim 29 further comprising acquiring measures of abdominal activity during void activity via electromyography electrodes in furtherance of determining detrusor pressure.

34. The method of claim 29 further comprising providing an isolation tubing extension for operatively uniting said catheter balloon adaptor with said pressure sensor.

35. The method of claim 29 further comprising selectively ceasing fluid discharge via said indwelling urinary catheter during either of bladder emptying events in furtherance of simulating a urethral resistance effect and thereafter establishing vesical pressure outlet resistance-urine flow rate relationships.

* * * * *